United States Patent
Liu et al.

(10) Patent No.: US 12,338,494 B2
(45) Date of Patent: *Jun. 24, 2025

(54) REAGENT AND METHOD FOR FLUORESCENCE QUANTITATIVE REAL-TIME PCR DETECTION OF RCL

(71) Applicant: ABELZETA INC., Rockville, MD (US)

(72) Inventors: Fang Liu, Shanghai (CN); Liping Lan, Shanghai (CN); Yutian Wei, Shanghai (CN); Xun Ye, Shanghai (CN); Li Zhang, Shanghai (CN); Jiaqi Huang, Rockville, MD (US); Yihong Yao, Rockville, MD (US)

(73) Assignee: ABELZETA INC., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/321,141

(22) Filed: May 22, 2023

(65) Prior Publication Data

US 2023/0287495 A1    Sep. 14, 2023

Related U.S. Application Data

(63) Continuation of application No. 16/967,659, filed as application No. PCT/CN2019/072576 on Jan. 21, 2019, now Pat. No. 11,697,848.

(30) Foreign Application Priority Data

Feb. 5, 2018 (CN) .......................... 201810114113.2

(51) Int. Cl.
| | |
|---|---|
| C12Q 1/68 | (2018.01) |
| C12Q 1/686 | (2018.01) |
| C12Q 1/6876 | (2018.01) |
| C12Q 1/70 | (2006.01) |

(52) U.S. Cl.
CPC .......... *C12Q 1/6876* (2013.01); *C12Q 1/686* (2013.01); *C12Q 1/70* (2013.01)

(58) Field of Classification Search
None
See application file for complete search history.

(56) References Cited

U.S. PATENT DOCUMENTS

| | | | | |
|---|---|---|---|---|
| 2004/0208849 | A1* | 10/2004 | Bell ........................ | C12N 15/86 424/93.2 |
| 2011/0070586 | A1* | 3/2011 | Slezak ................... | C12Q 1/701 435/6.14 |
| 2015/0376612 | A1* | 12/2015 | Lee ....................... | C12N 15/113 435/375 |

OTHER PUBLICATIONS

Lowe, T. et al. A computer program for selection of oligonucleotide primers for polymerase chain reaction. Nucleic Acids Research, vol. 18, No. 7, p. 1757-1761, (1990).*

* cited by examiner

*Primary Examiner* — Suryaprabha Chunduru
(74) *Attorney, Agent, or Firm* — Leason Ellis LLP

(57) ABSTRACT

The present invention provides a reagent and method for detecting a replication-competent lentivirus (RCL) by fluorescence quantitative real-time polymerase chain reaction (PCR). In particular, the present invention provides a primer and probe combination for detecting RCL, and a method for performing detection using said primer and probe; the present invention also provides a reagent kit comprising said primer and probe. The primer and probe combination of the present invention detects RCL with high amplification efficiency and good specificity, and can be used for RCL detection and RCL monitoring of clinical patient peripheral blood samples which may occur during a production process.

7 Claims, No Drawings
Specification includes a Sequence Listing.

REAGENT AND METHOD FOR FLUORESCENCE QUANTITATIVE REAL-TIME PCR DETECTION OF RCL

CROSS-REFERENCE TO RELATED APPLICATIONS

This is a U.S. national phase application under 35 U.S.C. § 371 of Patent Cooperation Treaty Application No. PCT/CN2019/072576, filed Jan. 21, 2019, which claims priority from Chinese Patent Application Serial No. 201810114113.2, filed on Feb. 5, 2018, and which incorporates by reference those PCT and Chinese applications in their entireties.

SEQUENCE LISTING

The instant application contains a Sequence Listing which has been filed electronically in ASCII format and is hereby incorporated by reference in its entirety. Said ASCII copy, created on Aug. 5, 2020, is named P2020-0958_amended_Sequence_listing_PN41046_SCBG01US.txt, and is 5,698 bytes in size.

TECHNICAL FIELD

The invention relates to the field of biological detection, and more specifically to a reagent and method for detecting RCL by fluorescence quantitative real-time PCR.

BACKGROUND

The biggest security risk in gene/cell therapy using lentivirus as a vector is the production of Replication Competent Lentivirus (RCL). Although the existing lentivirus production system has greatly reduced the possibility of RCL production, there is still a certain risk of RCL production, and an appropriate detection program is still needed to detect RCL. According to the recommendations in the FDA RCR Guidance issued by US FDA in 2006 and the FDA Recommendations issued in 2010, it is necessary to monitor RCL conditions for products and patient samples of gene/cell therapy using lentivirus as a vector. The detection methods recommended by FDA Recommendations include: 1) detection of RCL-related proteins; 2) detection of RCL-specific DNA sequences in samples using Quantitative real-time PCR (qPCR) method. The standard cell co-cultivation method for detecting RCL has a long cycle, and it takes about 6 weeks or longer to obtain experimental results.

TaqMan probe method is a highly specific quantitative PCR technology. The core is to use the 3'→5' exonuclease activity of Taq enzyme to cut off the probe to generate a fluorescent signal. Since the probe and the template are specifically bound, the intensity of the fluorescence signal represents the quantity of the templates. The FDA now allows the use of TaqMan probes, i.e. hydrolysis probes, qPCR method to quickly detect the RCL conditions in products. However, the current primers and probes for detecting RCL have the problems of low amplification efficiency and poor specificity. There is an urgent need in this field to develop new reagents and methods for detecting RCL by fluorescence quantitative real-time PCR.

SUMMARY OF THE INVENTION

The purpose of the present invention is to provide a reagent and method for detecting RCL by fluorescence quantitative real-time PCR.

More specifically, the purpose of the present invention is to provide a reagent and method for detecting the copy number of specific VSV-G gene of replication-competent lentivirus (RCL) by TaqMan fluorescence quantitative real-time PCR.

In a first aspect of the present invention, it provides a reagent combination comprising:
(i) a first primer pair for specific amplification of VSV-G gene and a first probe,
wherein, the first primer pair comprises: a first upstream primer with a sequence as shown in SEQ ID NO: 1, and a first downstream primer with a sequence as shown in SEQ ID NO: 2;
and, the first probe is shown in SEQ ID NO: 3; and/or
(ii) a second primer pair for specific amplification of VSV-G gene and a second probe,
wherein, the second primer pair comprises: a second upstream primer with a sequence as shown in SEQ ID NO: 4, and a second downstream primer with a sequence as shown in SEQ ID NO: 5;
and, the second probe is shown in SEQ ID NO: 6.

In another preferred embodiment, the reagent combination further comprises:
(iii) a third primer pair for specific amplification of a reference gene and a third probe,
wherein, the third primer pair comprises: a third upstream primer with a sequence as shown in SEQ ID NO: 27, and a third downstream primer with a sequence as shown in SEQ ID NO: 28;
and, the third probe is shown in SEQ ID NO: 29.

In another preferred embodiment, the probe is coupled with or has a detectable label.

In another preferred embodiment, the detectable label is selected from the group consisting of a chromophore, a chemiluminescent group, a fluorophore, an isotope and an enzyme.

In another preferred embodiment, the reagent combination is used for detecting Replication Competent Lentivirus (RCL).

In another preferred embodiment, the lentivirus uses Vesicular stomatitis virus-G protein (VSV-G) as the envelope protein.

In another preferred embodiment, the amplification efficiency of the reagent combination for detecting RCL is ≥90%, preferably ≥92%, and more preferably ≥95%.

In a second aspect of the present invention, it provides a PCR amplification system comprising: a buffer system for amplification and the primer combination of the first aspect of the present invention located in the system.

In a third aspect of the present invention, it provides a detection reagent comprising the primer combination of the first aspect of the present invention.

In another preferred embodiment, the detection reagent is used for detecting RCL.

In a fourth aspect of the present invention, it provides a detection kit comprising one or more containers, and the primer combination of the first aspect of the present invention located in the containers.

In another preferred embodiment, the detection kit is used for detecting RCL.

In another preferred embodiment, the first primer pair and the first probe are located in the same or different containers.

In another preferred embodiment, the second primer pair and the second probe are located in the same or different containers.

In another preferred embodiment, the third primer pair and the third probe are located in the same or different containers.

In another preferred embodiment, the third primer pair and the third probe are located in the same container as the first primer pair and the first probe.

In another preferred embodiment, the third primer pair and the third probe are located in the same container as the second primer pair and the second probe.

In another preferred embodiment, the kit further comprises reagents for amplification.

In another preferred embodiment, the reagents for amplification comprise a buffer, dNTP, and an amplification enzyme.

In another preferred embodiment, the kit further comprises an instruction manual.

In a fifth aspect of the present invention, it provides a detection method for detecting RCL, which comprises:
(a) providing a DNA sample to be tested;
(b) using the reagent combination of the first aspect of the present invention to perform fluorescence quantitative real-time PCR on the DNA sample to be tested; and
(c) calculating Cq value and VSV-G gene copy number of the DNA sample to be tested to determine whether the sample contains RCL.

In another preferred embodiment, the envelope protein of the RCL is Vesicular stomatitis virus-G protein (VSV-G).

In another preferred embodiment, the method is a TaqMan probe method.

In another preferred embodiment, in step (b), in a same amplification system, the first primer pair for specific amplification of VSV-G gene and the first probe are together used with the third primer pair for specific amplification of reference gene and the third probe, to perform fluorescence quantitative real-time PCR on the DNA sample to be tested.

In another preferred embodiment, in step (b), in a same amplification system, the second primer pair for specific amplification of VSV-G gene and the second probe are together used with the third primer pair for specific amplification of reference gene and the third probe, to perform fluorescence quantitative real-time PCR on the DNA sample to be tested.

In another preferred embodiment, in step (b), a positive control and a negative control are tested.

In another preferred embodiment, the method is a non-diagnostic and non-therapeutic method.

In another preferred embodiment, the method is an in vitro method.

In another preferred embodiment, in step (a), the DNA sample to be tested is extracted from a sample selected from the group consisting of: (i) a replication competent lentivirus, (ii) a biological product using lentivirus as a vector, and (iii) blood, bone marrow fluid, tissues and organs of human or an animal (such as a rodent, primate).

In another preferred embodiment, the human or animal described in (iii) has been administered with a biological product using lentivirus as a vector.

In another preferred embodiment, the lentivirus is a replication competent lentivirus.

In another preferred embodiment, the biological product using lentivirus as a vector is selected from the group consisting of:
Master Cell Bank (MCB), Working Cell Bank (WCB), End of Production (EOP) Cells, Vector-Containing Supernatant, Virus Infected Cells (Ex Vivo Transduced Cells), and a combination thereof.

It is to be understood that the various technical features of the present invention mentioned above and the various technical features specifically described hereinafter (as in the Examples) may be combined with each other within the scope of the present invention to constitute a new or preferred technical solution, which needs not be described one by one, due to space limitations.

MODES FOR CARRYING OUT THE PRESENT INVENTION

Through extensive and intensive research, the inventors have unexpectedly discovered for the first time a primer and probe combination for detecting RCL by fluorescence quantitative real-time PCR, and a method for performing detection using the primer and probe. The present invention also provides a reagent kit comprising the primer and probe. Experiments have shown that using the primer and probe combination of the present invention to detect RCL has high amplification efficiency and good specificity, and is suitable for clinical and laboratory detection. The present invention has been completed on the basis of this.

Specifically, the primer and probe combination of the present invention can be used for detection of RCL which may be produced during a production process and for RCL monitoring of clinical patient peripheral blood samples. The present invention also established and verified a method for detecting VSV-G sequence of a sample with the primer and probe combination of the present invention using the Taqman probe method, using human genomic DNA as background.

Vesicular stomatitis virus-fusion promoting envelope G protein (VSV-G) is a glycosylated membrane protein, which plays a decisive role in the two initial steps of virus entry into host cells: the attachment of the virus to the surface of the host cell and the pH-dependent endosomal membrane fusion induced by the virus.

VSV-G is an envelope protein with a wide host range, which can infect most human cells, and cells from species far away from humans such as zebrafish and drosophila. It is currently widely used in lentiviral vectors, and it can expand the infective lineage of lentiviral vectors. VSV-G plays an important role in gene and cell therapy.

TaqMan qPCR

TaqMan probe method is a highly specific quantitative PCR technology. The core is to use the 3'→5' exonuclease activity of Taq enzyme to cut off the probe to generate a fluorescent signal. Since the probe and the template are specifically bound, the intensity of the fluorescence signal represents the quantity of the templates.

The quantitative PCR reaction system of the TaqMan probe method comprises a pair of PCR primers and a probe. The probe only specifically binds to the template, and its binding site is between the two primers. The 5' end of the probe is labeled with a reporter group (Reporter, R) such as FAM™ amidites), (fluorescein VIC® (2'-chloro-7'-phenyl-1,4-dichloro-6-carboxyfluorescein), etc. The 3' end is labeled with a fluorescence quencher group (Quencher, Q), such as TAMRA™ (carboxytetramethylrhodamine), etc. When the probe is complete, the fluorescent energy emitted by the reporter group is absorbed by the quencher group, and an instrument cannot detect the signal. As the PCR progresses, Taq enzyme encounters the probe bound to the template during the chain extension process, and its 3'→5' exonuclease activity will cut off the probe. Therefore, the reporter group will be taken far away from the quencher group, and its energy will not be absorbed. That is, a fluorescent signal will be generated. Therefore, after each PCR cycle, the fluorescent signal also has a synchronous exponential growth process like the target fragment. The intensity of the signal represents the copy number of the template DNA.

As used herein, the term "probe" refers to a gene probe, that is, a nucleic acid probe, which is a nucleic acid sequence (DNA or RNA) complementary to the target gene with a detection label and a known sequence. The gene probe combines with the target gene through molecular hybridization to generate a hybridization signal, which can reveal the target gene from the vastest genome.

Reagent Combination

The present invention relates to a reagent combination for detecting RCL, comprising:
  (i) an upstream primer with the sequence shown in SEQ ID NO: 1, a downstream primer with the sequence shown in SEQ ID NO: 2 and a probe with the sequence shown in SEQ ID NO: 3 (that is, the VSV-G9 reagent combination as described below);
  or,
  (ii) an upstream primer with the sequence shown in SEQ ID NO: 4, a downstream primer with the sequence shown in SEQ ID NO: 5 and a probe with the sequence shown in SEQ ID NO: 6 (that is, the VSV-G8 reagent combination as described below).

The reagent combination of the present invention is used in the Taqman probe method to detect RCL, and has high amplification efficiency and good specificity.

Detection Method and Detection Kit

The present invention relates to a detection method for detecting RCL, wherein the method comprises: using the reagent combination of the first aspect of the present invention to perform fluorescence quantitative real-time PCR on a DNA sample to be tested; and calculating the Cq value and VSV-G gene copy number of the DNA sample to be tested to determine whether the sample contains RCL.

The method of the present invention can detect a sample selected from the group consisting of: (i) a replication competent lentivirus, (ii) a biological product using lentivirus as a vector, and (iii) blood, bone marrow fluid, tissues and organs of human or an animal (such as a rodent, primate).

The Main Advantages of the Present Invention Include:
  (a) Suitable for RCL detection during gene/cell therapy using lentiviral vector with VSV-G as envelope
  (b) High specificity and no specific response to genome background
  (c) Providing a duplex PCR method which can simultaneously detect reference gene The present invention will be further illustrated below with reference to the specific examples. It is to be understood that these examples are for illustrative purposes only and are not intended to limit the scope of the invention. For the experimental methods in the following examples the specific conditions of which are not specifically indicated, they are performed under routine conditions, e.g., those described by Sambrook et al., in Molecule Clone: A Laboratory Manual, New York: Cold Spring Harbor Laboratory Press, 1989, or as instructed by the manufacturers, unless otherwise specified. Unless indicated otherwise, parts and percentage are weight parts and weight percentage.

General Materials

1. Main Reagents

| Reagent name | Source | Item No. | Use |
| --- | --- | --- | --- |
| QIAamp DNA blood Midi kit | Qiagen | 51185 | For extracting cell or blood genomic DNA |
| Custom Taqman copy number analysis probe/primer-VSPCT_CDDJXJG | Thermo Fisher | Designed by the inventors | Primer/probe of VSV-G sequence |
| Taqman genotyping master mix kit | Thermo Fisher | 4304437 | For amplifying the target gene |
| C8166 Genomic DNA | C8166 cell extraction | The cells come from the CBMG production department, derived from ATCC | As genome background |
| Non-transduced human T cell genomic DNA | Non-transduced human T cell | The cells come from CBMG production department | As genome background |
| CBMG-PRM1 plasmid | The strains come from China Plasmid Vector Strain Cell Line Gene Collection Center (Biovector Science Lab, Inc.). After monoclonal selection and identification, amplification culture and | CBMG production department | Standard curve and positive control |

| Reagent name | Source | Item No. | Use |
|---|---|---|---|
| | plasmid purification were performed. | | |
| Diluent (for real-time PCR) | Takara | 9160 | For diluting plasmid to make standard curves |
| DNA suspension (10 mM Tris, 0.1m MEDTA, pH 8.0) | TEKNOVA | T0221 | For dissolving primers and probes, and for preparing storage solutions for primers and probes |

2. Primer and Probe Information

VSV-G1 to VSV-G4 primers were synthesized by GenScript, and the probes were synthesized by Invitech (VSV-G2 was not included).

VSV-G5 and VSV-G6 primers and probes were synthesized by GenScript.

VSV-G7 to VSV-G10 primers and robes were synthesized b Invitech.

| VSV-G1 | 5' to 3' sequence | SEQ ID NOs |
|---|---|---|
| Forward primer | CGAGATGGCTGATAAGGATCTC | SEQ ID NO: 7 |
| Reverse primer | ATTGATTATGGTGAAAGCAGGAC | SEQ ID NO: 8 |
| Probe | 6 FAM-TGCTGCAGCCAGATTCCCTGAATG-TAMARA | SEQ ID NO: 9 |

VSV-G1 primers and probes were designed with reference to Escarpe P I Zayek N, Chin P, Borellini F, Zufferey R, Veres G, and Kiermer V, Development of a sensitive assay for detection of replication-competent recombinant lentivirus in large-scale HIV-based vector preparations, *Mol Ther.* 2003 August; 8(2):332-41.

| VSV-G3 | 5' to 3' sequence | SEQ ID NOs |
|---|---|---|
| Forward primer | GACCTCAGTGGATGTAAG | SEQ ID NO: 10 |
| Reverse primer | CTGGAGAGATTGGAAGAC | SEQ ID NO: 11 |
| Probe | 6 FAM-CTAATTCAGGACGTT-MGB | SEQ ID NO: 12 |

| VSV-G4 | 5' to 3' sequence | SEQ ID NOs |
|---|---|---|
| Forward primer | GCAAGGAAAGCATTGAAC | SEQ ID NO: 13 |
| Reverse primer | CTGGACAATCACTGCTTC | SEQ ID NO: 14 |
| Probe | 6 FAM-CATCCGTCACAGTTGC-MGB | SEQ ID NO: 15 |

| VSV-G5 | 5' to 3' sequence | SEQ ID NOs |
|---|---|---|
| Forward primer | CCAGAAGGGTCAAGTATC | SEQ ID NO: 16 |
| Reverse primer | CAGAGGGAATAATCCAAGA | SEQ ID NO: 17 |
| Probe | 6 FAM-TGCTCCATCTCAGACCTCAGT-BHQ1 | SEQ ID NO: 18 |

| VSV-G6 | 5' to 3' sequence | SEQ ID NOs |
|---|---|---|
| Forward primer | GCAAGGAAAGCATTGAAC | SEQ ID NO: 19 |
| Reverse primer | CCGTCACAGTTGCATATC | SEQ ID NO: 20 |
| Probe | 6 FAM-AACTTGGCTGAATCCAGGCTT-BHQ1 | SEQ ID NO: 21 |

| VSV-G7 (VSPCT_CDH49U6) | 5' to 3' sequence (catalogue No. 4400294, lot number: 3007087) | SEQ ID NOs |
|---|---|---|
| Forward primer | AGTCAGACTCCCATCAGGTGT | SEQ ID NO: 22 |
| Reverse primer | TTGACCCTTCTGGGCATTCAG | SEQ ID NO: 23 |
| Probe | 6 FAM-CCTTATCAGCCATCTCGAACCAG-MGB | SEQ ID NO: 24 |

| VSV-G8 (VSPCT_CDFVKPC) | 5′ to 3′ sequence | SEQ ID NOs |
|---|---|---|
| Forward primer | GGATGTGTCATGCTTCCAAATGG | SEQ ID NO: 4 |
| Reverse primer | GTGAAGGATCGGATGGAATGTGTTA | SEQ ID NO: 5 |
| Probe | 6 FAM-ACCAGCGGAAATCACAAGTAGTG-MGB | SEQ ID NO: 6 |

| VSV-G9 (VSPCT_CDDJXJG) | 5′ to 3′ sequence | SEQ ID NOs |
|---|---|---|
| Forward primer | GAAAGGGAACTGTGGGATGACT | SEQ ID NO: 1 |
| Reverse primer | GAACTGGTCCTCAGAACTCCATT | SEQ ID NO: 2 |
| Probe | 6 FAM-CATATGAAGACGTGGAAATTGGACCC-MGB | SEQ ID NO: 3 |

RPP30 and TERT primers were synthesized by GenScript. RPP30 and TERT probes were synthesized b Invitech.

| RPP30 | 5' to 3' sequence | SEQ ID NOs |
|---|---|---|
| Forward primer | GTGGTAGTGCATAGACTTTA | SEQ ID NO: 25 |
| Reverse primer | GAGGACATTTGAGGAGTG | SEQ ID NO: 26 |
| Probe | VIC-CATCCGTCACAGTTGC-TAMARA | SEQ ID NO: 27 |

| TERT | 5′ to 3′ sequence | SEQ ID NOs |
|---|---|---|
| Forward primer | GGATCTTGTAGATGTTGG | SEQ ID NO: 28 |
| Reverse primer | TCCCAGAGAGGTTTCTAC | SEQ ID NO: 29 |
| Probe | VIC-CTGTTCACCTAGAGTCGCCAAG-TAMARA | SEQ ID NO: 30 |

4. C8166 Cell Line

The C8166 cell line is a human leukemia cell, which is liable to lentivirus infection and entry. It was used as a susceptible host of lentivirus in the RCL detection by cell co-culture method, which is conducive to the replication and amplification of low-level RCL.

5. Standard

The standard was used for preparing standard curves to establish a quantitative relationship between the quantification cycle (Cq) and the copy number. In the present program, the CBMG-PRM1 plasmid containing the VSV-G sequence was doubly diluted and 100 ng of human genomic DNA was added as a background, then the mixture was used as a standard.

6. Quality Control-Negative Control (NC)

Negative control standards include: No template control (NTC), which only lacks template in the qPCR reaction system for detecting the presence of dimer and reagent contamination; background negative control (BNC), using C8166 genomic DNA (gDNA) or human non transduced T cell (hNT) gDNA as the template in the qPCR reaction system for detecting the influence of gDNA on qPCR amplification, which can also be used for monitoring the contamination of reagents and sample loading process.

7. Quality Control-Positive Control (PC)

The quality control-positive control is the background gDNA of the same concentration (set as 100 ng in the present experiment) containing different copy numbers of CBMG-PRM1 plasmids. Quality control-positive control is used for evaluating the performance of the experiment.

General Methods

Screening of VSV-G Primers/Probes by TaqMan qPCR Method

Screening criteria: 1) Correlation coefficient ($R^2$) ≥0.99; 2) Amplification efficiency (Efficiency): 90%-110%; 3) No amplification of NTC and BNC.

qPCR Detection Experiment Process

1. Genomic DNA Extraction, Quality Control and Preservation (1) The genomic DNA was extracted from $2\times10^6$ cells/tube of cells with reference to the operation manual of QIAamp DNA blood Midi Extraction Kit;

(2) The DNA concentration and OD260/280 value were detected by NanoDrop 2000. The genomic DNA concentrations of the sample to be tested and the human cells (including C8166 cells and hNT) used as the genomic background were adjusted to 25 ng/μl. If the DNA concentration was on the high side, enzyme-free $H_2O$ was added for dilution. If the concentration is on the low side, a vacuum centrifugal concentrator was used to concentrate. The genomic DNA stock solution and 25 ng/μl was cryopreserved at −80° C.

2. Plasmid Dilution (1) The copy numbers of the plasmid per microliter of stock solutions were calculated according to the formula: $(6.02\times10^4)\times$(ng/μl))/(DNA length×660)=copies/μl;

(2) The plasmid solutions were diluted to $10^{10}$ copies/3 stock solution;

(3) The $10^{10}$ copies/μl stock solution was sub packaged in 11 μl/tube and cryopreserved at −80° C. to avoid repeated freezing and thawing.

|  |  | | | | | | | | | | |
|---|---|---|---|---|---|---|---|---|---|---|---|
|  | Concentration of the plasmid solution to be prepared copies/μl | $10^9$ | $10^8$ | $10^7$ | $10^6$ | $10^5$ | $10^4$ | $10^3$ | $10^2$ | 10 | 0 |
| Dilution process | diluent added/μl | 90 | 90 | 90 | 90 | 90 | 90 | 90 | 90 | 90 | 40 |
|  | Concentration of the plasmid solution added copies/μl | $10^{10}$ | $10^9$ | $10^8$ | $10^7$ | $10^6$ | $10^5$ | $10^4$ | $10^3$ | $10^2$ | — |
|  | Volume of the plasmid solution added/μl | 10 | 10 | 10 | 10 | 10 | 10 | 10 | 10 | 10 | — |
|  | Remarks | For example, to prepare $10^8$ copies/μl plasmid solution, 90 μl diluent was added to a 1.5 ml tube; $10^9$ copies/μl plasmid solution was mixed and centrifuged, from which 10 μl plasmid solution was taken and added to the 1.5 ml centrifuge tube and mixed, thus obtaining the $10^8$ copies/μl plasmid solution. | | | | | | | | | | |

3. Quality Control-Positive Control

The following quality control-positive controls are required in this method validation:

| Quality control-positive control(_copies plasmid + 100 ng C8166gDNA) | Use | Assay times (each assay was repeated 3 times) |
|---|---|---|
| 1 | Sensitivity experiment | 20 |
| 2 | Sensitivity experiment | 20 |
| 5 | Sensitivity experiment | 20 |
| 10 | Sensitivity experiment, lowest quantitative line experiment | 40 |
| 20 | Sensitivity experiment, lowest quantitative line experiment | 40 |
| 50 | Lowest quantitative line experiment | 20 |
| 100 | Lowest quantitative line experiment, repeatability experiment, reproducibility experiment, accuracy experiment | 36 |
| 200 | Lowest quantitative line experiment, repeatability experiment, reproducibility experiment, accuracy experiment | 20 |
| $10^4$ | Repeatability experiment, reproducibility experiment, accuracy experiment | 16 |
| $10^6$ | Repeatability experiment, reproducibility experiment, accuracy experiment | 16 |

The above quality control-positive controls were diluted in one batch and then sub packaged in 15 μl/tube/test and cryopreserved at −80° C. to avoid repeated freezing and thawing.

4. Doubling Dilution of the Standard

The following reagents were taken from −80° C. refrigerator and placed at 4° C. after thawing: $10^{10}$ copies/μl CBMG-PRM1 plasmid stock solution, $10^{10}$ copies pUC57-TERT plasmid stock solution, $10^{10}$ copies/μl pUC57-RPP30 plasmid stock solution, T cell gDNA (C8166 gDNA or hNTgDNA), quality control-positive control;

4.1 Doubling Dilution of CBMG-PRM1 Plasmid+Background Genomic DNA Standard (Single Plasmid Standard)

(1) According to the method shown in the following table, the standards were diluted in a 1.5 ml centrifuge tube with diluent in turn and centrifuged in a micro centrifuge; the operations were taken place on ice and the products were placed at C for use to obtain CBMG-PRM1 plasmid solutions of different concentrations/copy numbers:

Note: When single CBMG-PRM1 plasmid is used as a standard, and no gDNA is used as a background control, step (1) is sufficient.

(2) The above-mentioned plasmid solutions of different concentrations were taken to prepare CBMG-PRM1 plasmid+100 ng gDNA standard solutions in 1.5 ml centrifuge tubes according to the method shown in the following table, centrifuged with a micro centrifuge, operated on ice, and placed at 4° C. for use to obtain standard solutions of different concentrations:

|  |  | Standard solution number | | | | | | |
|---|---|---|---|---|---|---|---|---|
|  |  | Std6 | Std5 | Std4 | Std3 | Std2 | Std1 | BNC |
| Dilution process | Volume of gDNA added/μl | 16 | 16 | 16 | 16 | 16 | 16 | 16 |
|  | Concentration of the plasmid solution added copies/μl | $10^6$ | $10^5$ | $10^4$ | $10^3$ | $10^2$ | 10 | 0 |
|  | Volume of the plasmid solution added/μl | 4 | 4 | 4 | 4 | 4 | 4 | 4 |
|  | Remarks | For example, to prepare the standard solution Std6, 16 μl of gDNA solution was added to a 1.5 ml centrifuge tube, then 4 μl of plasmid solution with a concentration of $10^6$ copies/μl was added and mixed. | | | | | | |

4.2 Doubling Dilution of Double-Plasmid Standard (Containing VSV-G Plasmids and Reference Gene Plasmids, No Background gDNA)

According to the method shown in the following table, the standards were diluted in 1.5 ml centrifuge tubes with diluent in turn and centrifuged in a micro centrifuge; the operation was taken place on ice and the products were placed at 4° C. for use to obtain double-plasmid standard solutions of different concentrations/copy numbers:

|  |  | Standard solution number | | | | | | | | | | |
| --- | --- | --- | --- | --- | --- | --- | --- | --- | --- | --- | --- | --- |
|  |  | — | — | — | Std6 | Std5 | Std4 | Std3 | Std2 | Std1 | Std0 | B |
|  | Concentration of the plasmid solution to be prepared copies/µl | $10^9$ | $10^8$ | $10^7$ | $10^6$ | $10^5$ | $10^4$ | $10^3$ | $10^2$ | 10 | 1 | 0 |
| Dilution process | diluent added/µl | 80 | 90 | 90 | 90 | 90 | 90 | 90 | 90 | 90 | 90 | 90 |
|  | Concentration of CBMG-PRM1 plasmid solution added copies/µl | $10^{10}$ | $10^9$ | $10^8$ | $10^7$ | $10^6$ | $10^5$ | $10^4$ | $10^3$ | $10^2$ | 10 | — |
|  | Concentration of pUC57-RPP30 plasmid solution added copies/µl | $10^{10}$ | $10^9$ | $10^8$ | $10^7$ | $10^6$ | $10^5$ | $10^4$ | $10^3$ | $10^2$ | 10 | — |
|  | Volume of the plasmid solution added/µl | 20 | 10 | 10 | 10 | 10 | 10 | 10 | 10 | 10 | 10 | — |
|  | Remarks | To prepare $10^9$ copies/µl plasmid solution, 80 µl of diluent was added to an EP tube; 10 µl of CBMG-PRM1 plasmid solution and pUC57-RPP30 plasmid solution ($10^{10}$ copies/µl) were taken and added to the EP tube and mixed, respectively, thus obtaining the $10^9$ copies/µl plasmid solution. To prepare $10^8$ copies/µl plasmid solution, 90 µl of diluent was added to an EP tube; 10 µl solution of $10^9$ copies/µl containing CBMG-PRM1 plasmids and pUC57-RPP30 plasmids were added to the EP tube and mixed, thus obtaining the $10^8$ copies/µl plasmid solution. | | | | | | | | | | |

5. Preparation of Reaction System (Mix)

5.1 Preparation of CBMG-PRM1 Plasmid+100 ng gDNA Reaction System (Including the Standard and Quality Control-Positive Control) (Mix-VSV-G)

| Solution | 1× | ( n + n × 10%)× |
| --- | --- | --- |
| 2× Taqman genotyping master mixture | 10 µl | µl |
| 20 × VSV-G primer/probe Mix | 1 µl | µl |
| Template (1 µl CBMG-PRM1 plasmid + 4 µl gDNA) | 5 µl | — |
| H$_2$O | 4 µl | µl |
| Total volume | 20 µl | µl | n = test × 3
Template loading volume: 5 µl/well

The above solutions were added to 1.5 ml centrifuge tubes, operated on ice, mixed upside down, centrifuged in a micro centrifuge, and placed at 4° C. for use.

5.2 Preparation of Sample VSV-G Target Gene Detection Reaction System (Mix-Sample)

| Solution | 1× | ( n + n × 10%)× |
| --- | --- | --- |
| 2× Taqman genotyping master mixture | 10 µl | µl |
| 20 × VSV-G primer/probe Mix | 1 µl | µl |
| Template (gDNA from sample) | 8 µl | — |
| H$_2$O | 1 µl | µl |
| Total volume | 20 µl | µl | n = test × 3
Template loading volume: 8 µl/well, i.e. 200 ng/well

The above solutions were added to 1.5 ml centrifuge tubes, operated on ice, mixed upside down, centrifuged in a micro centrifuge, and placed at 4° C. for use.

5.3 Preparation of Reference Gene Standard Curve Detection Reaction System (Mix-Reference-Std)

| Solution | 1× | ( n + n × 10%)× |
| --- | --- | --- |
| 2× Taqman genotyping master mixture | 10 µl | µl |
| 20 × RPP30 or TERT primer/probe mix | 1 µl | µl |
| Template (1 µl pUC57-RPP30 or pUC57-TERT plasmid) | 1 µl | — |
| H$_2$O | 8 µl | µl |
| Total volume | 20 µl | µl | n = test × 3
Loading volume of template: 1 µl/well

The above solutions were added to 1.5 ml centrifuge tubes, operated on ice, mixed upside down, centrifuged in a micro centrifuge, and placed at 4° C. for use.

5.4 Preparation of Reference Gene Sample Detection Reaction System (M-Mix-Reference)

| Solution | 1× | ( n + n × 10%)× |
| --- | --- | --- |
| 2× Taqman genotyping master mixture | 10 µl | µl |
| 20 × RPP30 or TERT primer/probe mix | 1 µl | µl |
| Template (1 µl pUC57-RPP30 or pUC57-TERT plasmid) | 1 µl | — |
| H$_2$O | 8 µl | µl |
| Total volume | 20 µl | µl | n = test × 3
Template loading volume: 1 µl/well, i.e. 25 ng/well

The above solutions were added to 1.5 ml centrifuge tubes, operated on ice, mixed upside down, centrifuged in a micro centrifuge, and placed at 4° C. for use.

5.5 Preparation of Double-Plasmid Standard Duplex qPCR Reaction System

| Solution | 1× | (n + n × 10%)× |
|---|---|---|
| 2× Taqman genotyping master mixture | 10 μl | μl |
| 20 × VSV-G primer/probe Mix | 1 μl | μl |
| 20 × Reference Primer/Probe Mix | 1 μl | μl |
| Template (CBMG-PRA3 plasmid + pUC57-RPP30 plasmid) | 1 μl | — |
| H₂O | 7 μl | μl |
| Total volume | 20 μl | μl | n = test × 3

Loading volume of template: 1 μl/well

The above solutions were added to 1.5 ml centrifuge tubes, operated on ice, mixed upside down, centrifuged in a micro centrifuge, and placed at 4° C. for use.

5.6 Preparation of Single Plasmid Standard Duplex qPCR Reaction System

| Solution | 1× | (n + n × 10%)× |
|---|---|---|
| 2× Taqman genotyping master mixture | 10 μl | μl |
| 20 × VSV-G primer/probe Mix | 1 μl | μl |
| 20 × Reference Primer/Probe Mix | 1 μl | μl |
| Template (CBMG-PRA3 plasmid) | 1 μl | μl |
| gDNA background (C8166 or NT, 1000 ng) | X μl | μl |
| H₂O | X μl | μl |
| Total volume | 20 μl | μl |

Loading volume of template: 1 μl/well

The above solutions were added to 1.5 ml centrifuge tubes, operated on ice, mixed upside down, centrifuged in a micro centrifuge, and placed at 4° C. for use.

6. qPCR Detection 6.1 Single-Plex qPCR Detection (1) According to the following table, 15 μl of the above-prepared reaction system "Mix-VSV-G", 12 μl of "Mix-Sample" were taken and added to a 96-well PCR reaction plate, and 19 μl of "Mix-Reference-Std" and "Mix-Reference" were added to the 96-well PCR reaction plate;

| | 1 | 2 | 3 | 4 | 5 | 6 | 7 | 8 | 9 | 10 | 11 | 12 |
|---|---|---|---|---|---|---|---|---|---|---|---|---|
| A | NTC | NTC | NTC | | | | | | | | | |
| B | BNC | BNC | BNC | | | | | | | | | |
| C | Std1 | Std1 | Std1 | PC | PC | PC | | sample | sample | sample | | |
| D | Std2 | Std2 | Std2 | | | | | | | | | |
| E | Std3 | Std3 | Std3 | | | | | | | | | |
| F | Std4 | Std4 | Std4 | | | | | | | | | |
| G | Std5 | Std5 | Std5 | | | | | | | | | |
| H | Std6 | Std6 | Std6 | | | | | | | | | |

Std: CBMG-PRM1 plasmids + 100 ng gDNA standard or pUC57-RPP30 or pUC57-TERT plasmids;
NTC: No Template Control;
BNC: Background Negative Control;

PC: Positive control (___copies CBMG-PRM1 plasmid + 100 ng gDNA)

(2) The standards: std6, std5, std4, std3, std2, std1, and NC or PC were added to the corresponding wells in sequence, the detection of VSV-G standard curve was 5 μl/well; the detection of "sample to be tested" VSV-G was 8 μl/well and sequentially added to the corresponding well; the detection of reference gene curve and the "sample to be tested" were both 1 μl/well.

(3) The 96-well PCR reaction plate was blocked with sealing membrane, then centrifuged at 200×g for 2 minutes;

(4) the plate was placed into Quant Studio Dx real-time PCR, and the reaction conditions for Taqman Universal PCR Master Mix was set as follows:

Standard Conditions:
  UNG incubation: 2 min at 50° C.
  Polymerase activation: 10 min at 95° C.
  PCR: 40 cycles
    Degeneration: 15 sec at 95° C.
    Annealing/Extension: 60 sec at 60° C.

6.2 Detection of Double-Plasmid Standard Duplex qPCR (1) According to the following table, 19 μl of the duplex PCR reaction system "Std" prepared above was added to the 96-well PCR reaction plate;

|   | 1 | 2 | 3 | 4 | 5 | 6 | 7 | 8 | 9 | 10 | 11 | 12 |
|---|---|---|---|---|---|---|---|---|---|---|---|---|
| A | NTC | NTC | NTC | | | | | | | | | |
| B | Std0 | Std0 | Std0 | | | | | | | | | |
| C | Std1 | Std1 | Std1 | PC | PC | PC | | sample | sample | sample | | |
| D | Std2 | Std2 | Std2 | | | | | | | | | |
| E | Std3 | Std3 | Std3 | | | | | | | | | |
| F | Std4 | Std4 | Std4 | | | | | | | | | |
| G | Std5 | Std5 | Std5 | | | | | | | | | |
| H | Std6 | Std6 | Std6 | | | | | | | | | |

Std: Standard containing CBMG-PRM1 plasmids and pUC57-RPP30 plasmids;
NTC: No template control;

(2) The standards std6, std5, std4, std3, std2, std1, std0 and blank control B were added to the corresponding wells in sequence with 1 μl/well;
(3) The 96-well PCR reaction plate was blocked with sealing membrane, then centrifuged at 200×g for 2 minutes;
(4) The plate was place into Quant Studio Dx real-time PCR, and the reaction conditions for Taqman genotyping master mixture was set as follows:

Standard Conditions:
Polymerase activation: 10 min at 95° C.
PCR: 40 cycles
Degeneration: 15 sec at 95° C.
Annealing/Extension: 60 sec at 60° C.

7. Experimental Data Quality Control Parameters
(1) Amplification efficiency 90%~110%;
(2) Standard curve for the standard $R^2 \geq 0.99$;
(3) Negative controls include NTC and BNC: at least 2 repeated wells among the 3 repeated wells have no amplification, i.e. Cq>40, if 1 repeated well has amplification, Cq need to be >average $Cq_{LOD}$ (mean $Cq_{LOD}$).
If any one of the above 3 points does not meet the requirements, the experiment needs to be repeated.

8. Data Processing and Analysis
(1) After the reaction, a standard curve was outputted by software, which was composed of at least 5 points;

9. Result Judgment of RCL Detection
According to the standard curve, the Cq value of each sample and the VSV-G gene copy number of 100 ng genome was outputted by software automatically;
In order to facilitate the determination of the positive and negative results of RCL, the copy number of LOD+100 ng C8166 gDNA was used as the quality control-positive control (PC) in the experiment. The average Cq value of each experiment was used as the positive threshold.

| No. | qPCR results | RCL status | Pass/Fail | solution |
|---|---|---|---|---|
| 1 | 3 out of 3 repeats contain undetectable VSV-G | Negative | Pass | NA |
| 2 | 2 out of 3 repeats contain undetectable VSV-G, 1 detectable, Cq > average $Cq_{LOD\ as\ pc}$ | Negative | Pass | NA |
| 3 | 1 out of 3 repeats contains undetectable VSV-G, 2 detectable, Cq > average $Cq_{LOD\ as\ pc}$ | Negative | Pass | NA |
| 4 | 1 out of 3 repeats contains undetectable VSV-G, 2 detectable, Cq ≤ average $Cq_{LOD\ as\ pc}$ | Initial positive | Fail | Repeat; The result of repeated qPCR needs to meet No.1-No.3 |
| 5 | Repeated qPCR: 1 out of 3 | Positive | Fail | Cell-based RCL |

-continued

| No. | qPCR results | RCL status | Pass/Fail | solution |
|---|---|---|---|---|
| | repeats contains undetectable VSV-G, 2 detectable, Cq ≤ average $Cq_{LOD\ as\ pc}$ | | | detection was performed by a third party |

Example 1

Screening of Primer/Probe Pairs for the Reference Gene

Doubly diluted 293T gDNA was used for making standard curve, to test two primer/probe pairs RPP30 and TERT.
The results are shown in Table 1. The amplification efficiency of RPP30 was 99.24%, and the amplification efficiency of TERT was 83.22%.

TABLE 1

Concentrations of two primer/probe pairs of reference gene and the result parameter information

| Primer/probe name | Primer (μM) | Probe (μM) | Threshold value | Amplification efficiency | $R^2$ |
|---|---|---|---|---|---|
| TERT | 0.4 | 0.2 | 0.04 | 83.22% | 0.997 |
| RPP30 | 0.4 | 0.2 | 0.05 | 99.24% | 0.985 | pUC57-RPP30 plasmid doubling dilution was used for making a standard curve once again to test the effectiveness of RPP30 primer/probe. The results showed that the amplification efficiency of RPP30 primer/probe was 93.77%, and $R^2$ was 0.995. Follow-up experiments were conducted with primer/probe pairs of RPP30.

Example 2

Screening of Probe/Primer Pairs for VSV-G Gene Detection

Doubly diluted 293T gDNA was used to make standard curve, to test VSV-G1, VSV-G3, VSV-G4, VSV-G5, VSV-G6, VSV-G7, VSV-G8, VSV-G9 primer/probe pairs.
The results are shown in Table 2. From the perspective of amplification efficiency, the amplification efficiencies of VSV-G4, VSV-G6, VSV-G8, and VSV-G9 are between 90% and 110%. However, the background of VSV-G6 was relatively high. When only 293T gDNA was used as the background template, the Cq value was 38.6. While the sensitivity of VSV-G4 was relatively low. When the VSV-G template was 10 copies, the Cq value was 39.2, when $10^6$ copies, the Cq value is 21.8. The sensitivity of VSV-G1 was also relatively low. The Cq value was 38.3 when the VSV-G template was 10 copies.

Table 2 the concentration of each VSV-G primer/probe pair and the result parameter informations with 293T gDNA as background control

TABLE 2 the concentration of each VSV-G primer/probe pair and the result parameter informations with 293T gDNA as background control

| Primer/Probe name | Primer (μM) | Probe (μM) | Threshold value | Amplification efficiency | $R^2$ | 0 (293T gDNA) background | Cq value (10 copies of VSV-G templates) |
|---|---|---|---|---|---|---|---|
| VSV-G1 | 0.9 | 0.25 | 0.068 | 93.68% | 0.994 | ND* | 38.3 |
| VSV-G3 | 0.8 | 0.4 | 0.04 | 88.41% | 0.986 | ND | 38.6 |
| VSV-G4 | 0.8 | 0.4 | 0.08 | 91.15% | 0.987 | 39.43 | 39.2 |
| VSV-G5 | 0.8 | 0.25 | 0.04 | 52.33% | 0.984 | ND | ND |
| VSV-G6 | 0.9 | 0.25 | 0.08 | 94.73% | 0.997 | 38.6 | 36.6 |
| VSV-G7 | 0.9 | 0.25 | 0.08 | 88.81% | 0.996 | ND | 37.0 |
| VSV-G8 | 0.9 | 0.25 | 0.1 | 94.97% | 0.998 | ND | 35.9 |
| VSV-G9 | 0.9 | 0.25 | 0.1 | 92.70% | 0.999 | ND | 37.0 |

*ND means not detectable, that is, not detected

CAR-NCgDNA and C8166 gDNA were used as background templates respectively. The amplification efficiencies, $R^2$ and background conditions of VSV-G6, VSV-G8, VSV-G9 primers/probes were detected again.

The results with CAR-NCgDNA as a background control are shown in Table 3. The results with C8166gDNA as a background are shown in Table 4. The results showed that VSV-G6 primer/probe and 293T gDNA had non-specific binding and amplification. VSV-G8 and VSV-G9 primers/probes had good specificity under three genomic backgrounds: 293T, C8166, and NC (non-transduced T cells), and the amplification efficiencies were also 90%~110%. In the subsequent double probes/primers test, VSV-G8 and VSV-G9 primers/probes were used for testing.

Example 3

Detection of the Amplification Efficiency of VSV-G Primer/Probe and Reference Gene Primer/Probe in the Same Reaction Well by Double-Plasmid Method The VSV-G plasmids (CBMG-PRM1) and the reference gene plasmids (pUC57-RPP30) were doubly diluted by 10 times and placed in a same well as a template to establish a standard curve. Duplex PCR was performed to detect the interference of the two probe/primer pairs. In this example, the combination of VSV-G8 and internal reference RPP30 and the combination of VSV-G9 and internal reference RPP30 were tested.

TABLE 3

Concentrations of VSV-G6, VSV-G8, VSV-G9 primer/probe pairs and the result parameters with CAR-NCgDNA as background control

| Primer/Probe name | Primer (μM) | Probe (μM) | Threshold value | Amplification efficiency | $R^2$ | 0 (NC gDNA) background | Cq value (10 copies of VSV-G templates) |
|---|---|---|---|---|---|---|---|
| VSV-G6 | 0.8 | 0.25 | 0.1 | 90.04% | 0.993 | ND | 37.7 |
| VSV-G8 | 0.9 | 0.25 | 0.1 | 94.55% | 0.995 | ND | 36.5 |
| VSV-G9 | 0.9 | 0.25 | 0.1 | 96.95% | 0.999 | ND | 35.8 |

TABLE 4

Concentrations of VSV-G6, VSV-G8, VSV-G9 primer/probe pairs and the result parameters with C8166gDNA as background control

| Primer/probe name | Primer (μM) | Probe (μM) | Threshold value | Amplification efficiency | $R^2$ | 0 (C8166 gDNA) background | Cq value (10 copies of VSV-G templates) |
|---|---|---|---|---|---|---|---|
| VSV-G6 | 0.8 | 0.25 | 0.08 | 91.72% | 0.997 | ND | 37.1 |
| VSV-G8 | 0.9 | 0.25 | 0.1 | 96.30% | 0.998 | ND | 35.8 |
| VSV-G9 | 0.9 | 0.25 | 0.1 | 90.68% | 0.999 | ND | 37.0 |

The results are shown in Table 5. In the duplex PCR reaction of the VSV-G8/RPP30 primer probe combination, neither the amplification of VSV-G8 nor the amplification of RPP30 was significantly affected. In the duplex PCR reaction of the VSV-G9/RPP30 primer probe combination, neither the amplification of VSV-G9 nor the amplification of RPP30 was significantly affected.

The result parameters of the two probe/primer pairs detected by duplex PCR are as follows:

| combination | Primer/Probe name | Primer (mM) | Probe (mM) | Threshold value | Amplification efficiency | $R^2$ | Cq value (10 copies of VSV-G templates) |
|---|---|---|---|---|---|---|---|
| VSV-G8/ | VSV-G8 | 0.9 | 0.25 | 0.1 | 92.90% | 0.986 | 37.3 |
| RPP30 | RPP30 | 0.4 | 0.2 | 0.04 | 101.35% | 0.986 | 37.6 |
| VSV-G9/ | VSV-G9 | 0.9 | 0.25 | 0.1 | 101.80% | 0.991 | 35.2 |
| RPP30 | RPP30 | 0.4 | 0.2 | 0.04 | 94.79% | 0.998 | 37.4 |

Example 4

Detection of Double Primer/Probe PCR Reaction Under Single Plasmid+High-Quality Background Single plasmid was used for making standard curve. VSV-G gene copy number detection was performed by duplex PCR detection under high-quality background (C8166 and NT, 1000 ng). The amplification efficiencies of the VSV-G primer/probe and reference gene primer/probe and the effect of high-quality background on duplex PCRVSV-G were tested in the same reaction well.

The results are shown in Table 6. The amplification efficiencies of VSV-G8 and VSV-G9 were relatively high under the background of high-quality genome, and the amplification efficiency of VSV-G9 is higher.

TABLE 6 the results of two pairs of probe/primer pairs detected by duplex PCR with 1000 ng C8166 and NT gDNA as background

| Background | combination | Primer/probe name | Primer (mM) | Probe (mM) | Threshold value | Amplification efficiency | $R^2$ | Cq value (10 copies of VSV-G templates) |
|---|---|---|---|---|---|---|---|---|
| C8166 gDNA | VSV-G8/RPP30 | VSV-G8 | 0.9 | 0.25 | 0.1 | 92.12% | 0.995 | 37.0 |
| | | RPP30 | 0.4 | 0.2 | 0.04 | — | — | — |
| | VSV-G9/RPP30 | VSV-G9 | 0.9 | 0.25 | 0.1 | 93.53% | 0.994 | 36.7 |
| | | RPP30 | 0.4 | 0.2 | 0.04 | — | — | — |
| NT gDNA | VSV-G8/RPP30 | VSV-G8 | 0.9 | 0.25 | 0.1 | 85.17% | 0.989 | 38.1 |
| | | RPP30 | 0.4 | 0.2 | 0.04 | — | — | — |
| | VSV-G9/RPP30 | VSV-G9 | 0.9 | 0.25 | 0.1 | 96.98% | 0.997 | 35.6 |
| | | RPP30 | 0.4 | 0.2 | 0.04 | — | — | — |

All literatures mentioned in the present application are incorporated herein by reference, as though each one is individually incorporated by reference. In addition, it should also be understood that, after reading the above teachings of the present invention, those skilled in the art can make various changes or modifications, equivalents of which falls in the scope of claims as defined in the appended claims.

The invention claimed is:

1. A reagent combination comprising:
(i) a first primer pair for specific amplification of vesicular stomatitis virus G protein (VSV-G) gene and a first probe, wherein, the first primer pair comprises: a first forward primer consisting of the sequence of SEQ ID NO: 1, and a first reverse primer consisting of the sequence of SEQ ID NO: 2;
wherein the first probe consists of the sequence of SEQ ID NO: 3 and a first detectable label; or
(ii) a second primer pair for specific amplification of VSV-G gene and a second probe, wherein, the second primer pair comprises: a second forward primer consisting of the sequence of SEQ ID NO: 4, and a second reverse primer consisting of the sequence of SEQ ID NO: 5;
wherein the second probe consists of the sequence of SEQ ID NO: 6 and a second detectable label; and further comprises
a third primer pair for specific amplification of a reference gene and a third probe,
wherein, the third primer pair comprises: a third forward primer consisting of the sequence of SEQ ID NO: 25, and a third reverse primer consisting of the sequence of SEQ ID NO: 26;
and, the third probe consists of the sequence of SEQ ID NO: 27 and a third detectable label.

2. The reagent combination of claim 1, wherein the amplification efficiency of the reagent combination for detecting replication competent lentivirus (RCL) is ≥90%.

3. A detection kit comprising the reagent combination of claim 1.

4. The detection kit of claim 3, wherein the kit further comprises reagents for amplification.

5. The reagent combination of claim 2, wherein the amplification efficiency of the reagent combination for detecting replication competent lentivirus (RCL) is ≥92%.

6. The reagent combination of claim 2, wherein the amplification efficiency of the reagent combination for detecting replication competent lentivirus (RCL) is ≥95%.

7. The reagent combination of claim 1, wherein the first, second and third detectable labels are fluorophores.

* * * * *

SEQUENCE LISTING

```
Sequence total quantity: 30
SEQ ID NO: 1            moltype = DNA  length = 22
FEATURE                 Location/Qualifiers
misc_feature            1..22
                        note = Primer
source                  1..22
                        mol_type = other DNA
                        organism = synthetic construct
SEQUENCE: 1
```

```
gaaagggaac tgtgggatga ct                                              22

SEQ ID NO: 2           moltype = DNA  length = 23
FEATURE                Location/Qualifiers
misc_feature           1..23
                       note = Primer
source                 1..23
                       mol_type = other DNA
                       organism = synthetic construct
SEQUENCE: 2
gaactggtcc tcagaactcc att                                             23

SEQ ID NO: 3           moltype = DNA  length = 26
FEATURE                Location/Qualifiers
misc_feature           1..26
                       note = Probe
source                 1..26
                       mol_type = other DNA
                       organism = synthetic construct
SEQUENCE: 3
catatgaaga cgtggaaatt ggaccc                                          26

SEQ ID NO: 4           moltype = DNA  length = 23
FEATURE                Location/Qualifiers
misc_feature           1..23
                       note = Primer
source                 1..23
                       mol_type = other DNA
                       organism = synthetic construct
SEQUENCE: 4
ggatgtgtca tgcttccaaa tgg                                             23

SEQ ID NO: 5           moltype = DNA  length = 25
FEATURE                Location/Qualifiers
misc_feature           1..25
                       note = Primer
source                 1..25
                       mol_type = other DNA
                       organism = synthetic construct
SEQUENCE: 5
gtgaaggatc ggatggaatg tgtta                                           25

SEQ ID NO: 6           moltype = DNA  length = 23
FEATURE                Location/Qualifiers
misc_feature           1..23
                       note = Probe
source                 1..23
                       mol_type = other DNA
                       organism = synthetic construct
SEQUENCE: 6
accagcggaa atcacaagta gtg                                             23

SEQ ID NO: 7           moltype = DNA  length = 22
FEATURE                Location/Qualifiers
misc_feature           1..22
                       note = Primer
source                 1..22
                       mol_type = other DNA
                       organism = synthetic construct
SEQUENCE: 7
cgagatggct gataaggatc tc                                              22

SEQ ID NO: 8           moltype = DNA  length = 23
FEATURE                Location/Qualifiers
misc_feature           1..23
                       note = Primer
source                 1..23
                       mol_type = other DNA
                       organism = synthetic construct
SEQUENCE: 8
attgattatg gtgaaagcag gac                                             23

SEQ ID NO: 9           moltype = DNA  length = 24
FEATURE                Location/Qualifiers
misc_feature           1..24
                       note = Probe
source                 1..24
                       mol_type = other DNA
                       organism = synthetic construct
```

-continued

```
SEQUENCE: 9
tgctgcagcc agattccctg aatg                                              24

SEQ ID NO: 10           moltype = DNA  length = 18
FEATURE                 Location/Qualifiers
misc_feature            1..18
                        note = Primer
source                  1..18
                        mol_type = other DNA
                        organism = synthetic construct
SEQUENCE: 10
gacctcagtg gatgtaag                                                     18

SEQ ID NO: 11           moltype = DNA  length = 18
FEATURE                 Location/Qualifiers
misc_feature            1..18
                        note = Primer
source                  1..18
                        mol_type = other DNA
                        organism = synthetic construct
SEQUENCE: 11
ctggagagat tggaagac                                                     18

SEQ ID NO: 12           moltype = DNA  length = 15
FEATURE                 Location/Qualifiers
misc_feature            1..15
                        note = Probe
source                  1..15
                        mol_type = other DNA
                        organism = synthetic construct
SEQUENCE: 12
ctaattcagg acgtt                                                        15

SEQ ID NO: 13           moltype = DNA  length = 18
FEATURE                 Location/Qualifiers
misc_feature            1..18
                        note = Primer
source                  1..18
                        mol_type = other DNA
                        organism = synthetic construct
SEQUENCE: 13
gcaaggaaag cattgaac                                                     18

SEQ ID NO: 14           moltype = DNA  length = 18
FEATURE                 Location/Qualifiers
misc_feature            1..18
                        note = Primer
source                  1..18
                        mol_type = other DNA
                        organism = synthetic construct
SEQUENCE: 14
ctggacaatc actgcttc                                                     18

SEQ ID NO: 15           moltype = DNA  length = 16
FEATURE                 Location/Qualifiers
misc_feature            1..16
                        note = Probe
source                  1..16
                        mol_type = other DNA
                        organism = synthetic construct
SEQUENCE: 15
catccgtcac agttgc                                                       16

SEQ ID NO: 16           moltype = DNA  length = 18
FEATURE                 Location/Qualifiers
misc_feature            1..18
                        note = Primer
source                  1..18
                        mol_type = other DNA
                        organism = synthetic construct
SEQUENCE: 16
ccagaagggt caagtatc                                                     18

SEQ ID NO: 17           moltype = DNA  length = 19
FEATURE                 Location/Qualifiers
misc_feature            1..19
                        note = Primer
source                  1..19
                        mol_type = other DNA
```

-continued

```
                            organism = synthetic construct
SEQUENCE: 17
cagagggaat aatccaaga                                                    19

SEQ ID NO: 18              moltype = DNA  length = 21
FEATURE                    Location/Qualifiers
misc_feature               1..21
                           note = Probe
source                     1..21
                           mol_type = other DNA
                           organism = synthetic construct
SEQUENCE: 18
tgctccatct cagacctcag t                                                 21

SEQ ID NO: 19              moltype = DNA  length = 18
FEATURE                    Location/Qualifiers
misc_feature               1..18
                           note = Primer
source                     1..18
                           mol_type = other DNA
                           organism = synthetic construct
SEQUENCE: 19
gcaaggaaag cattgaac                                                     18

SEQ ID NO: 20              moltype = DNA  length = 18
FEATURE                    Location/Qualifiers
misc_feature               1..18
                           note = Primer
source                     1..18
                           mol_type = other DNA
                           organism = synthetic construct
SEQUENCE: 20
ccgtcacagt tgcatatc                                                     18

SEQ ID NO: 21              moltype = DNA  length = 21
FEATURE                    Location/Qualifiers
misc_feature               1..21
                           note = Probe
source                     1..21
                           mol_type = other DNA
                           organism = synthetic construct
SEQUENCE: 21
aacttggctg aatccaggct t                                                 21

SEQ ID NO: 22              moltype = DNA  length = 21
FEATURE                    Location/Qualifiers
misc_feature               1..21
                           note = Primer
source                     1..21
                           mol_type = other DNA
                           organism = synthetic construct
SEQUENCE: 22
agtcagactc ccatcaggtg t                                                 21

SEQ ID NO: 23              moltype = DNA  length = 21
FEATURE                    Location/Qualifiers
misc_feature               1..21
                           note = Primer
source                     1..21
                           mol_type = other DNA
                           organism = synthetic construct
SEQUENCE: 23
ttgacccttc tgggcattca g                                                 21

SEQ ID NO: 24              moltype = DNA  length = 23
FEATURE                    Location/Qualifiers
misc_feature               1..23
                           note = Probe
source                     1..23
                           mol_type = other DNA
                           organism = synthetic construct
SEQUENCE: 24
ccttatcagc catctcgaac cag                                               23

SEQ ID NO: 25              moltype = DNA  length = 20
FEATURE                    Location/Qualifiers
misc_feature               1..20
                           note = Primer
source                     1..20
```

```
                    mol_type = other DNA
                    organism = synthetic construct
SEQUENCE: 25
gtggtagtgc atagacttta                                      20

SEQ ID NO: 26       moltype = DNA   length = 18
FEATURE             Location/Qualifiers
misc_feature        1..18
                    note = Primer
source              1..18
                    mol_type = other DNA
                    organism = synthetic construct
SEQUENCE: 26
gaggacattt gaggagtg                                        18

SEQ ID NO: 27       moltype = DNA   length = 16
FEATURE             Location/Qualifiers
misc_feature        1..16
                    note = Probe
source              1..16
                    mol_type = other DNA
                    organism = synthetic construct
SEQUENCE: 27
catccgtcac agttgc                                          16

SEQ ID NO: 28       moltype = DNA   length = 18
FEATURE             Location/Qualifiers
misc_feature        1..18
                    note = Primer
source              1..18
                    mol_type = other DNA
                    organism = synthetic construct
SEQUENCE: 28
ggatcttgta gatgttgg                                        18

SEQ ID NO: 29       moltype = DNA   length = 18
FEATURE             Location/Qualifiers
misc_feature        1..18
                    note = Primer
source              1..18
                    mol_type = other DNA
                    organism = synthetic construct
SEQUENCE: 29
tcccagagag gtttctac                                        18

SEQ ID NO: 30       moltype = DNA   length = 22
FEATURE             Location/Qualifiers
misc_feature        1..22
                    note = Probe
source              1..22
                    mol_type = other DNA
                    organism = synthetic construct
SEQUENCE: 30
ctgttcacct agagtcgcca ag                                   22
```